(12) United States Patent
Root (10) Patent No.: US 9,216,263 B2
(45) Date of Patent: Dec. 22, 2015

(54) BREATH INTAKE VALVE (71) Applicant: David H. Root, Penfield, NY (US)

(72) Inventor: David H. Root, Penfield, NY (US)

( * ) Notice: Subject to any disclaimer, the term of this patent is extended or adjusted under 35 U.S.C. 154(b) by 0 days.

(21) Appl. No.: 14/313,084

(22) Filed: Jun. 24, 2014

(65) Prior Publication Data

US 2014/0305440 A1    Oct. 16, 2014

Related U.S. Application Data (63) Continuation-in-part of application No. 13/068,704, filed on May 18, 2011, now Pat. No. 8,800,565.

(60) Provisional application No. 61/395,802, filed on May 19, 2010.

(51) Int. Cl.
*A61M 11/00* (2006.01)
*A61M 16/04* (2006.01)
*A61F 2/20* (2006.01)
*A61M 16/20* (2006.01)

(52) U.S. Cl.
CPC ............ *A61M 16/0468* (2013.01); *A61F 2/203* (2013.01); *A61M 16/208* (2013.01); *A61M 2205/183* (2013.01); *A61M 2205/581* (2013.01)

(58) Field of Classification Search
CPC .......... A61M 16/0468; A61M 16/208; A61M 16/04; A61M 16/0465; A61M 2/203; A61M 2205/183; A61M 2205/581
USPC ........................................ 128/207.15–207.17
See application file for complete search history.

(56) References Cited

U.S. PATENT DOCUMENTS

| | | | |
|---|---|---|---|
| 3,844,290 A | 10/1974 | Birch et al. | |
| 4,040,428 A | 8/1977 | Clifford | |
| 4,054,153 A | 10/1977 | Guyton | |
| 4,207,884 A | 6/1980 | Isaacson | |
| 4,538,607 A | 9/1985 | Saul | |
| 4,759,356 A | 7/1988 | Muir | |
| 5,391,205 A | 2/1995 | Knight | |
| 5,765,560 A | 6/1998 | Verkerke et al. | |
| 6,193,751 B1 | 2/2001 | Singer | |
| 6,358,222 B1 | 3/2002 | Grundei | |
| 6,668,831 B1 | 12/2003 | Hegwood | |
| 7,025,784 B1 | 4/2006 | Blom et al. | |
| 7,240,676 B2 * | 7/2007 | Rutter | 128/207.16 |
| 7,387,216 B1 | 6/2008 | Smith | |
| 2005/0139266 A1 | 6/2005 | Partridge | |
| 2006/0266359 A1 | 11/2006 | Beurden et al. | |
| 2009/0194108 A1 | 8/2009 | Newman | |
| 2012/0097168 A1 | 4/2012 | Perez et al. | |

\* cited by examiner

*Primary Examiner* — Steven Douglas (57) ABSTRACT

A breath intake valve is connected to a tracheostomy tube inserted into a patient's trachea. The inner end of the valve attaches to the tracheostomy tube. An apertured disk endpiece with an O-ring around its circumference is releasably set into the outer end of the tubular valve body. A floppy diaphragm overlying the inner face of the disk endpiece functions as an intake valve to allow patient inhalation and air intake, and as a check valve to block patient exhalation, thereby to redirect it to the patient's larynx, sinuses, and mouth for normal speech. The O-ring gives way to forceful patient exhalation to release the disk endpiece from the tubular valve body. The disk endpiece is tethered to the breath intake valve body to prevent misplacement of the endpiece after such a release. The breath intake valve is itself likewise tethered to the tracheostomy tube to prevent its misplacement after any disconnection. The breath intake valve also includes a whistle to produce audible signal when exhalation is forceful.

13 Claims, 6 Drawing Sheets

BREATH INTAKE VALVE

This application claims priority from and is a continuation-in-part of U.S. patent application Ser. No. 13/068,704 for a BREATH INTAKE VALVE FOR A TRACHEOSTOMY TUBE, filed May 18, 2011 by David H. Root, which further claimed priority from U.S. Provisional Patent Application 61/395,802, filed May 19, 2010 by David H. Root, both of which are hereby incorporated by reference in their entirety.

The embodiments disclosed herein are directed to a breath intake valve for use with a tracheostomy tube.

BACKGROUND AND SUMMARY

The disclosed embodiments are directed to a breath intake valve for a tracheostomy tube. Specifically, the embodiments are directed to an improvement of various speaking valves currently available from Passy-Muir and other companies.

A tracheotomy (or tracheostomy) involves placement of a breathing tube into an incision through the windpipe. The typical speaking valve relates to a valve placed on an external free end of a breathing tube to assist a tracheostomy patient's speech. The valve is typically a unidirectional air valve or check valve, and allows air intake into the patient's trachea, and it blocks exhalation, thereby redirecting exhaled air to the patient's larynx, epiglottis, sinuses, and mouth to permit normal speech.

In summary, the disclosed embodiments are directed to a breath intake valve for connection with a tracheostomy tube inserted into a patient's trachea. The inner end of the valve attaches to the tracheostomy tube. An apertured disk endpiece, with an O-ring around its circumference, is releasably set into the outer end of the tubular valve body. A floppy diaphragm overlying the inner face of the disk endpiece functions as an intake valve to allow patient inhalation and air intake, and as a check valve to block patient exhalation, thereby redirecting it to the patient's larynx, sinuses, and mouth for normal speech. The O-ring gives way to forceful patient exhalation to release the disk endpiece from the tubular valve body. The disk endpiece is tethered to the tubular valve body to prevent its misplacement after such a release. The valve is itself likewise tethered to the tracheostomy tube to prevent its misplacement after any disconnection. The breath intake valve may also include a whistle to produce an audible signal when exhalation is forceful.

Disclosed in embodiments herein is a breath intake valve for connection with a tracheostomy tube inserted into a patient's trachea, said breath intake valve including: a tubular valve body including an inner end for connection with said tracheostomy tube, and an outer end; an one of a plurality of apertured disk endpieces disposed within said outer end of said valve body, said each disk endpiece including a circumferential concave O-ring seat, and an O-ring disposed in said O-ring seat for sealing engagement with said tubular valve body, wherein each of the apertured disk endpieces has a different circumferential concave O-ring seat; a breath intake valve flap operatively connected to said disk endpiece on the inner side thereof, said valve flap being responsive to patient inhalation to open said disk endpiece for air intake through said tracheostomy tube into the patient's trachea, and responsive to patient exhalation to close said disk endpiece to thereby redirect said exhalation to the patient's larynx, sinuses, and mouth for normal speech; and a hinge operatively associating the breath intake valve with the tracheostomy tube such that when removed from the valve body, the breath intake tube remains attached to the tracheostomy tube yet permitting access to an interior of the tracheostomy tube; said disk endpiece and said O-ring responsive to exhalation pressure above a release pressure level to release said disk endpiece from said tubular body, thereby to permit exhalation through said intake valve.

Further disclosed in embodiments herein is a breath intake valve for connection with a tracheostomy tube, said breath intake valve including: a tubular valve body including an inner end for connection with said tracheostomy tube, and an outer end; an apertured disk endpiece disposed within said outer end of said valve body, said disk endpiece including a removable O-ring in an O-ring seat around the outer circumference of said disk endpiece for circumferential engagement with the interior of said tubular valve body; a breath intake valve flap operatively connected to said disk endpiece on the inner side thereof, said valve flap being responsive to patient inhalation to open said disk endpiece for air intake to the patient through said tracheostomy tube, and responsive to patient exhalation to close said disk endpiece, thereby to redirect said exhalation to the patient's larynx, sinuses, and mouth; said disk endpiece and said O-ring being responsive to exhalation pressure above a preselected release pressure level to release said disk endpiece from said tubular body, thereby to permit exhalation through said valve, wherein said disk endpiece includes a circumferential O-ring seat suitable for receiving one of a plurality of O-rings having different characteristics and to thereby establish a desired endpiece release pressure for the breath intake valve.

Also disclosed herein is a method of avoiding pressure buildup and enabling deliberate exhalation in a tracheostomy patient having a tracheostomy tube, comprising: connecting a breath intake valve to the tracheostomy tube, said breath intake valve including: a tubular valve body including an inner end for connection with the tracheostomy tube, and an outer end; an apertured endpiece disposed within the outer end of said valve body, said endpiece including a removable O-ring in an O-ring seat adjacent the circumference of said endpiece, said O-ring engaging the interior of the tubular valve body; a breath intake valve flap operatively connected to said endpiece on an inner side thereof, said valve flap being responsive to the patient's inhalation to open for air intake to the patient through said tracheostomy tube, and to close in response to patient exhalation, thereby redirecting the exhalation to the patient's larynx; said disk endpiece and said O-ring responding to an exhalation pressure above a release pressure level to enable a release of said endpiece from said tubular body and permit exhalation through said intake valve; and installing an O-ring providing a desired endpiece release pressure for the patient on said O-ring seat.

The various embodiments described herein are not intended to limit the disclosure to those embodiments described. On the contrary, the intent is to cover all alternatives, modifications, and equivalents as may be included within the spirit and scope of the various embodiments and equivalents set forth. For a general understanding, reference is made to the drawings. In the drawings, like references have been used throughout to designate identical or similar elements. It is also noted that the drawings may not have been drawn to scale and that certain regions may have been purposely drawn disproportionately so that the features and aspects could be properly depicted.

DETAILED DESCRIPTION

Figure 1:
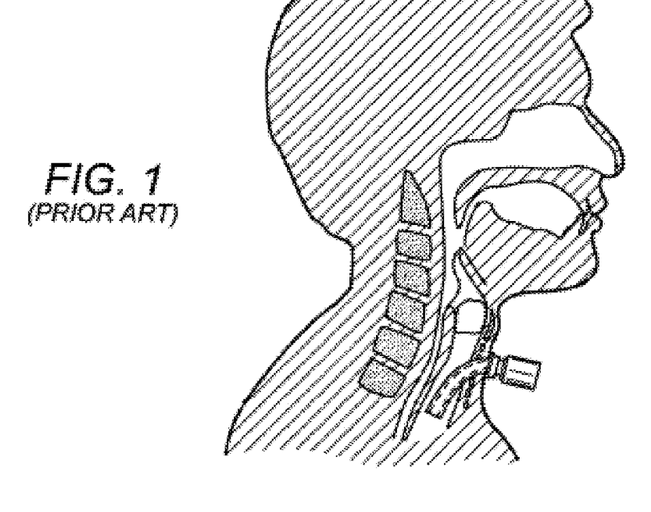
FIG. 1 represents a patient with a tracheostomy tube and associated breath intake valve.
Figure 2:
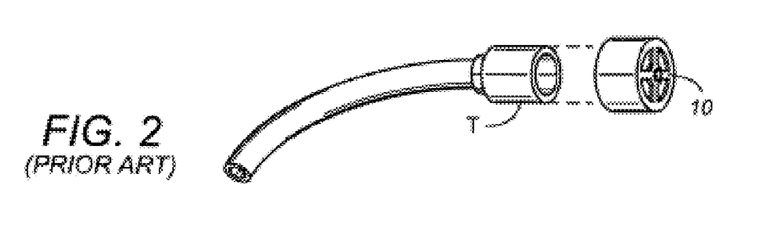
FIG. 2 is an exploded view of a prior art tracheostomy tube and associated breath intake valve.
Figure 3:
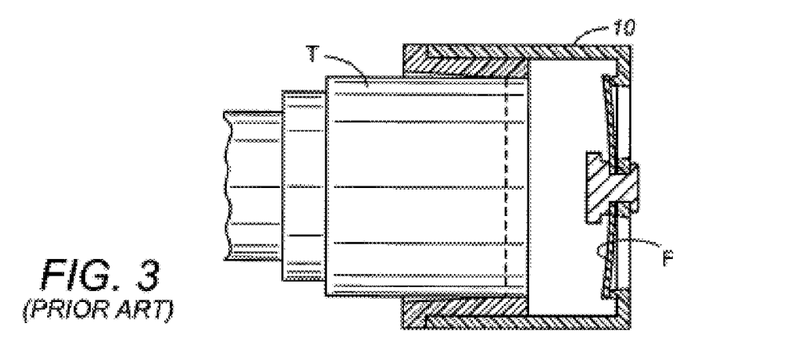
FIG. 3 is an enlarged sectional view of the breath intake valve of FIG. 2.

FIGS. 1-3 are believed to be representative of prior art. The component in FIGS. 1-3 which is relevant to a disclosed embodiment is the prior art breath intake valve 10. As a patient inhales, a valve flap F opens inward to allow inhalation through a breath intake tube T and into the patient. When the patient exhales, the valve flap F closes to prevent exhalation through the breath intake valve 10. Exhalation is instead directed up through the patient's larynx, epiglottis, sinuses, and mouth to enable the patient to speak. This is the desired respiration flow in a post-tracheostomy patient. However it is possible, and indeed has happened, that if the apparatus is improperly worn or incorrectly adjusted, the patient's exhalation can be totally blocked. Patients have fainted from this inability to exhale.

Figures 4, 5:
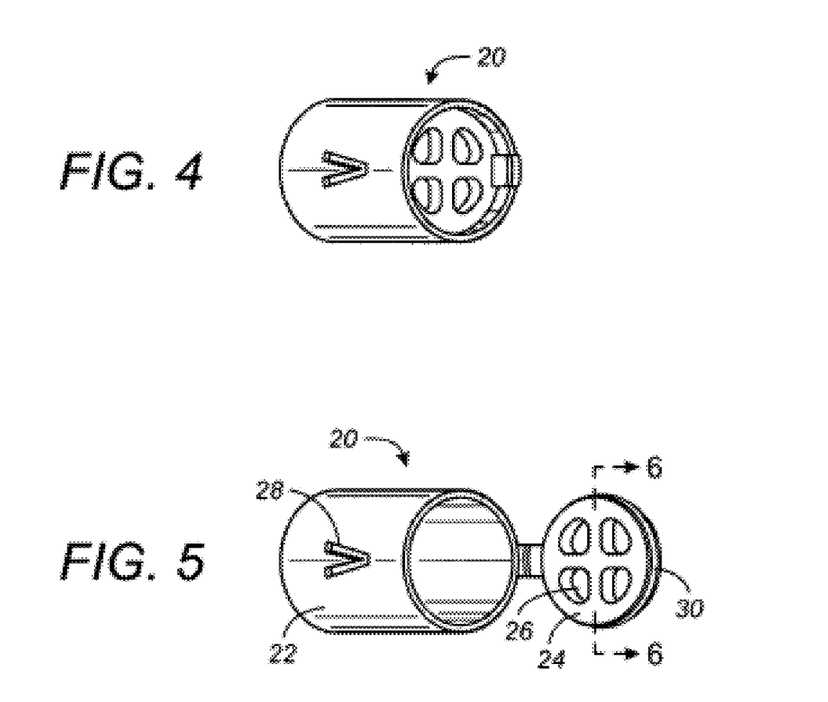
FIG. 4 shows a breath intake valve of this invention.
FIG. 5 shows the breath intake valve of FIG. 4 with its outer endpiece expelled.
Figure 6:
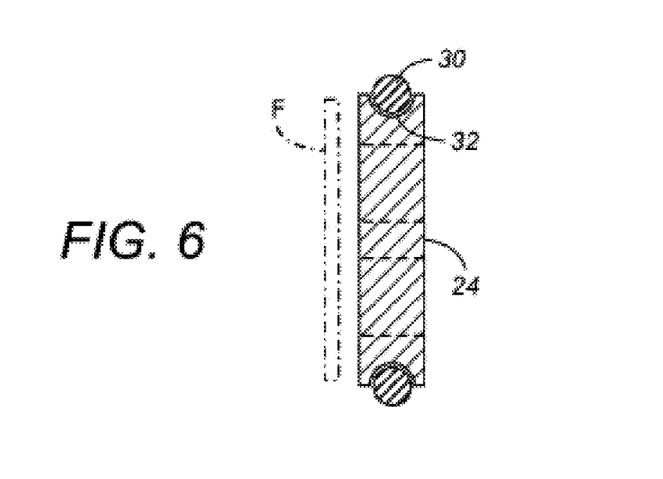
FIG. 6 is a sectional view of the intake valve endpiece, on the plane 6-6 of FIG. 5.

In FIGS. 4-6, a disclosed embodiment includes a breath intake valve 20 includes a cylindrical body 22, a disk endpiece 24 with air apertures 26 through it, and a resilient valve flap F, similar to that in FIG. 3, disposed adjacent to the inner face of the disk endpiece 24. Inner and outer faces of the disk endpiece 24 are shown in FIG. 5 and FIG. 6 respectively. The valve flap F is shown somewhat schematically in FIG. 6; in reality it is mounted adjacent to the inner face of the disk endpiece 24. The endpiece 24 is releasably fit into the outer end of the tubular valve body 22 by an O-ring 30, and is hinged or otherwise tethered to the body as shown in FIG. 5. It will be appreciated that in an alternative embodiment, the O-ring and endpiece may be similarly constructed as a cap to fit over the valve body 22, wherein the O-ring may be seated within an interior annular seat in the cap.

In normal operation the endpiece 24 remains in place (FIG. 4). If it becomes necessary for a patient to exhale through the valve 20, a deliberate exhalation will push the endpiece 24 open against a certain resistance provided by the O-ring 30. FIG. 5 shows the endpiece 24 in a break-open condition. The breath intake valve 20 (i.e., the combination valve body 22, endpiece 24, flap F, and O-ring 30) thus operates as an emergency relief valve.

Figure 9:
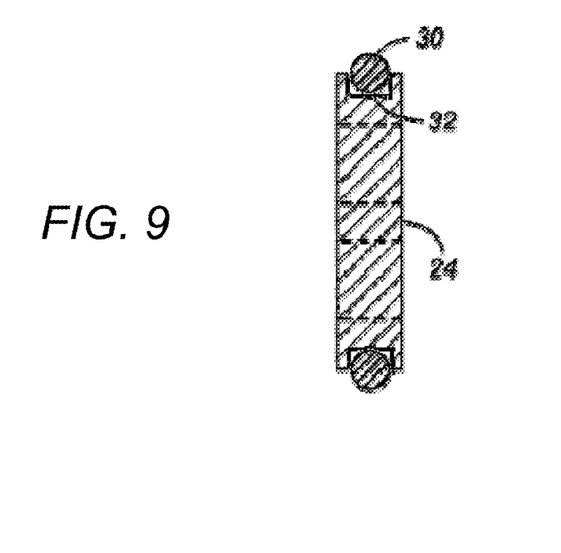
FIG. 9 is a sectional view of an alternative intake valve endpiece, on the plane 6-6 of FIG. 5.
Figure 10:
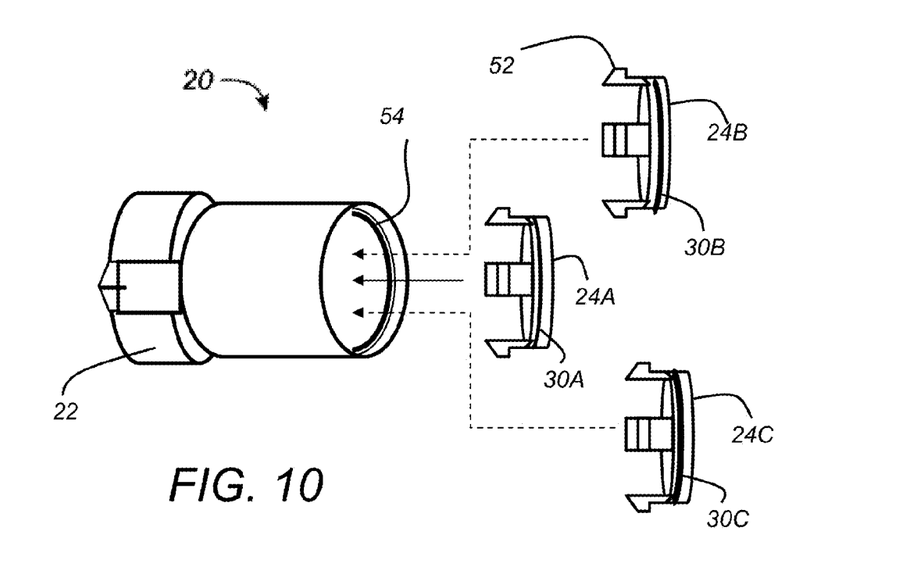
FIG. 10 is an assembly view of an alternative valve design, where a plurality of endpieces are provided to enable control of the blowoff pressure level.

FIG. 6 shows the endpiece 24 with a concave circumferential seat 32 for the O-ring 30, and a schematic representation of the valve flap F. "Deliberate exhalation" is meant as exhalation which is done consciously because it is done against some degree of resistance. The exhalation pressure required to release the endpiece is in the range of 10 to 20 centimeters of water. The O-ring 30 in a particular breath intake valve 20 is selected from among O-rings of different resilience, or of different minor radii, or O-rings placed in different amounts of recess in seat 32, thereby to establish a desired endpiece release pressure suitable for case-by-case application. In one embodiment, the seat depth may be approximately 0.60 mm, although the appropriate depth of the seat is also a function of the size (diameter and thickness) of the O-ring, and the material from which the O-ring is made. Thus, the depth of the seat may be from about 0.2 mm to 1.2 mm. Furthermore, the seat may have a concave or curved profile (cross-section) as illustrated, for example in FIG. 6. However, in an alternative embodiment, the seat 32 may have different profiles, including a flat bottom such as illustrated in FIG. 9. Different tracheostomy patients will require different endpiece release settings, depending on factors such as the patient's age, health, and strength. Hence, the breath intake valve may be provided with a plurality of endpieces and/or O-rings as depicted in FIG. 10, where O-rings 20A-C are progressively larger in thickness of the O-ring, so that the respiratory therapist or other medical professional may modify the release or blow-off setting of the valve to a level appropriate for the patient. As an alternative to changing O-rings, a plurality of endpieces may be provided, each with different O-rings and/or seat depths, etc. to vary the blowoff pressure. In the embodiment depicted in FIG. 10, each of the endpieces 24A-C also include fingers 52 that catch on an inner shoulder 54 inside of the valve body 22, to prevent the endpiece from being removed without manual intervention, but allowing sufficient space for the endpiece to separate from the end of the valve body and relieve pressure buildup.

The valve body 22 may further include a notch whistle 28, which sounds off when exhalation is attempted through the valve 20. This is a further safeguard to inform the patient or caregiver that the system needs to be reset.

In one embodiment, the valve body and associated components may be made of a plastic or polymeric material such as polypropylene (e.g., homopolymer propylene available from PolyOne Corp.), although alternative materials such as metals and ceramics may be similarly employed for the body or other components of the breath intake valve. Use of the plastic material is advantageous as it allows breath intake valve to be non-metallic and therefore suitable for use during magnetic-resonance imaging procedures. The plastic material also permits the components of the breath intake valve to be injection molded, and further enable the hinges to be constructed at the time of molding as "living" hinges between the component parts. Use of alternative materials may require the addition of hinge or similar connective materials to link the parts together. The O-rings are conventional O-rings, preferably made of a silicone-based elastomer or rubber material, which retains natural flexibility and resilience, and resists compression set. Thus, the characteristics of the O-ring (e.g., material, size, thickness, etc.) may be used to control the relative blow-off (relief) pressure for the breath intake valve 20.

Figure 7:
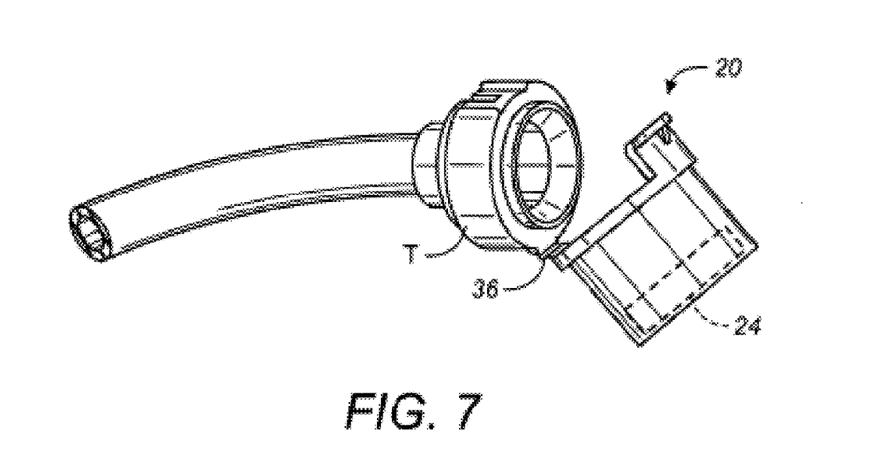
FIG. 7 is a view similar to FIG. 2 including a further improvement of this invention.

It may be necessary from time to time to remove the breath intake valve 20 from the intake tube T, to permit a procedure such as suctioning of fluids from the patient. In such an event it is customary to remove the breath intake valve 20 from the tube T, and set it down wherever convenient while the procedure is performed. For convenience and cleanliness, the disclosed embodiments have hinged the breath intake valve 20 to the intake tube T, as indicated in FIG. 7. When it is necessary to remove the breath intake valve 20, it is not necessary to find a place to set it down. The valve simply drops out of the way to permit the procedure, but remains conveniently attached to the tube T by its hinge 36 to simplify its reconnection when the procedure is completed.

Figure 8:
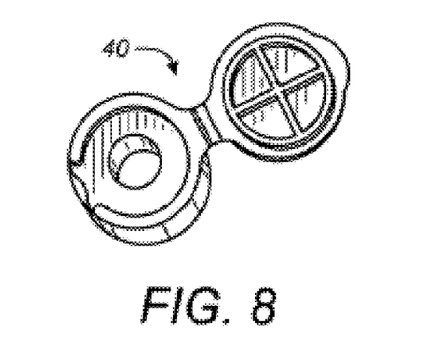
FIG. 8 shows a hinged cap for removable placement over the open end of the breath valve.

FIG. 8 shows a hinged cap 40 for removable placement over the end of the breath valve 20. Another advantage of having the hinge is for the use of an ambu-bag, commonly known as a resuscitation bag. When the hinge is in the open position there is a 'male end' toward the side of the tracheostomy tube. It will receive the 'female end' of the Ambu bag. This is very useful for the Respiratory Therapist as the patient may require what is known as pulmonary lavage. This procedure allows for the therapist to instill a normal saline liquid into the lungs and the use of the ambu-bag to penetrate the saline deep into the smaller parts of the lungs (bronchioles) to loosen phlegm and allow it to 'float' on the saline solution for easier extraction by the use of suctioning. This procedure allows for better oxygenation and tissue perfusion. Once again, the valve does not have to be removed but rather opened up, thus, reducing the chances of a nosocomial infection.

Figure 11:
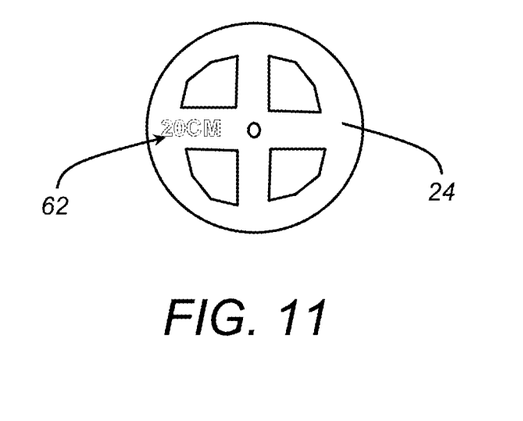
FIG. 11 is a top view of an alternative endpiece.
Figure 12:
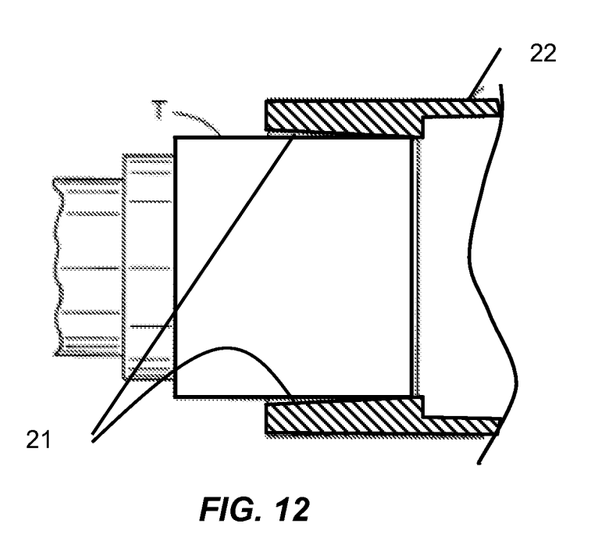
FIG. 12 shows a tubular valve body including an inner end with a variable inner-diameter.

Also contemplated are embodiments, such as that depicted in FIG. 11, where the endpiece 24 of breath intake valve 20 includes indicia molded or otherwise permanently embossed on the surface to characterize a relative pressure release level for that endpiece, whether the blowoff pressure be the result of the material and size of the O-ring and/or a combination with the seat depth or profile. It will also be appreciated that the inner-diameter of the valve body 22, on the end that is attached to a tracheostomy tube, may be made with a variable inside diameter to facilitate connection with tracheostomy tubes of different sizes. For example the tapered inner walls 21 as represented in FIG. 12, similar to those illustrated adjacent tube T in FIG. 3.

It should be understood that various changes and modifications to the embodiments described herein will be apparent to those skilled in the art. Such changes and modifications can be made without departing from the spirit and scope of the present disclosure and without diminishing its intended advantages. It is therefore anticipated that all such changes and modifications be covered by the instant application.

What is claimed is:

1. A breath intake valve for connection with a tracheostomy tube inserted into a patient's trachea, said breath intake valve including:
   a tubular valve body including an inner end for connection with said tracheostomy tube, and an outer end;
   one of a plurality of apertured disk endpieces disposed within said outer end of said valve body, each disk endpiece including a circumferential concave O-ring seat, and an O-ring disposed in said O-ring seat for sealing engagement with said tubular valve body, wherein each of the apertured disk endpieces has a different circumferential concave O-ring seat;
   a breath intake valve flap operatively connected to said disk endpiece on an inner side thereof, said valve flap being responsive to patient inhalation to open said disk endpiece for air intake through said tracheostomy tube into the patient's trachea, and responsive to patient exhalation to close said disk endpiece to thereby redirect said exhalation to the patient's larynx, sinuses, and mouth for normal speech; and
   a hinge operatively associating the breath intake valve with the tracheostomy tube such that when removed from the valve body, the breath intake tube remains attached to the tracheostomy tube yet permitting access to an interior of the tracheostomy tube;
   said disk endpiece and said O-ring responsive to exhalation pressure above a release pressure level to release said disk endpiece from said tubular body, thereby to permit exhalation through said intake valve.

2. The breath intake valve according to claim 1, wherein said O-ring is formed from a silicone rubber.

3. The breath intake valve according to claim 1, wherein a different circumferential concave O-ring seat depth for each endpiece produces a different relative pressure release level.

4. The breath intake valve according to claim 3, wherein each endpiece includes indicia molded on the surface thereof to characterize the relative pressure release level for that endpiece.

5. The breath intake valve according to claim 1, further including a variable inner-diameter on the inner end to facilitate connection with tracheostomy tubes of different sizes.

6. The breath intake valve according to claim 1, wherein the O-ring seat has a concave cross-section.

7. A breath intake valve for connection with a tracheostomy tube, said breath intake valve including:
   a tubular valve body including an inner end for connection with said tracheostomy tube, and an outer end;
   one of a plurality of apertured disk endpieces disposed within said outer end of said valve body, each disk endpiece including a removable O-ring in an O-ring seat around the outer circumference of the disk endpiece for circumferential engagement with an interior of said tubular valve body, wherein each of the apertured disk endpieces has a different O-ring, each exhibiting a different characteristic;
   a breath intake valve flap operatively connected to said disk endpiece on an inner side thereof, said valve flap being responsive to patient inhalation to open said disk endpiece for air intake to the patient through said tracheostomy tube, and responsive to patient exhalation to close said disk endpiece, thereby to redirect said exhalation to the patient's larynx, sinuses, and mouth;
   each disk endpiece and associated O-ring being responsive to exhalation pressure above a preselected release pressure level to release said disk endpiece from said tubular body, to thereby permit exhalation through said tubular valve body.

8. A method of avoiding pressure buildup and enabling deliberate exhalation in a tracheostomy patient having a tracheostomy tube, comprising:
   connecting a breath intake valve to the tracheostomy tube, said breath intake valve including:
      a tubular valve body including an inner end for connection with the tracheostomy tube, and an outer end;
      an apertured endpiece disposed within the outer end of said valve body, said endpiece including a removable O-ring in an O-ring seat adjacent the circumference of said endpiece, said O-ring engaging an interior of the tubular valve body;
      a breath intake valve flap operatively connected to said endpiece on an inner side thereof. said valve flap being responsive to the patient's inhalation to open for air intake to the patient through said tracheostomy tube, and to close in response to patient exhalation, thereby redirecting the exhalation to the patient's larynx;
      said disk endpiece and said O-ring responding to an exhalation pressure above a release pressure level to enable a release of said endpiece from said tubular body and permit exhalation through said intake valve;
   selecting, from a group of different endpieces, consisting essentially of endpieces having O-rings with different characteristics or endpieces having different circumferential O-ring seat depths, an endpiece to provide a desired release pressure for the patient; and installing a selected endpiece in the outer end of said valve body.

9. The breath intake valve according to claim 7, wherein the different O-ring characteristic includes O-ring material.

10. The breath intake valve according to claim 7, wherein the different O-ring characteristic includes O-ring size.

11. The breath intake valve according to claim 7, wherein the different O-ring characteristic includes O-ring thickness.

12. The breath valve according to claim 8 wherein the group of different endpieces are pre-assembled to provide a pre-determined release pressure.

13. The breath valve according to claim 12 wherein each endpiece includes indicia of the relative release pressure for the endpiece.

* * * * *